US00PP11389P

United States Patent [19]

Trees

[11] Patent Number: Plant 11,389

[45] Date of Patent: May 23, 2000

[54] GERANIUM PLANT NAMED 'BFP-1520'

[75] Inventor: Scott C. Trees, Nipomo, Calif.

[73] Assignee: Ball Floraplant, A Division of Ball Horticultural Co., West Chicago, Ill.

[21] Appl. No.: 09/114,060

[22] Filed: Jul. 10, 1998

[51] Int. Cl.[7] ..... A01H 5/00

[52] U.S. Cl. ..... Plt./330

[58] Field of Search ..... Plt./325, 328, 330, Plt./329

[56] References Cited

U.S. PATENT DOCUMENTS

| | | | |
|---|---|---|---|
| P.P. 4,039 | 4/1977 | Buck | Plt./327 |
| P.P. 5,059 | 6/1983 | Elsner | Plt./330 |
| P.P. 7,017 | 9/1989 | Klemm | Plt./330 |
| P.P. 7,385 | 11/1990 | Schumann | Plt./330 |
| P.P. 7,499 | 4/1991 | Schumann | Plt./330 |
| P.P. 8,288 | 6/1993 | Trees | Plt./330 |
| P.P. 9,762 | 12/1996 | Utecht | Plt./329 |

*Primary Examiner*—Howard J. Locker
*Assistant Examiner*—Kent L. Bell
*Attorney, Agent, or Firm*—C. A. Whealy

[57] ABSTRACT

A new and distinct cultivar of Geranium plant named 'BFP-1520', characterized by its numerous semi-double bright coral pink-colored flowers; upright and rounded growth habit, basal branching; and dark green leaves with a distinct zonation pattern.

1 Drawing Sheet

BACKGROUND OF THE INVENTION

The present invention relates to a new and distinct cultivar of Geranium plant, botanically known as *Pelargonium*× *hortorum*, and hereinafter referred to by the cultivar name 'BFP-1520'.

The new Geranium is a product of a planned breeding program conducted by the Inventor in Arroyo Grande, Calif. The objective of the breeding program was to develop new cultivars with excellent basal branching, medium growth habit, numerous flowers and umbels, and interesting flower and foliage colors.

The new Geranium originated from a cross made by the Inventor of the proprietary *Pelargonium*×*hortorum* selection 6762-1 as the male, or pollen parent, with the proprietary *Pelargonium*×*hortorum* selection 6875-8 as the female, or seed parent. The cultivar 'BFP-1520' was discovered and selected by the Inventor as a flowering plant within the progeny of the stated cross in a controlled environment in Arroyo Grande, Calif., on Sep. 15, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'BFP-1520'. These characteristics in combination distinguish 'BFP-1520' as a new and distinct cultivar:

1. Numerous semi-double bright coral pink-colored flowers.

2. Upright and rounded growth habit.

3. Basal branching.

4. Dark green leaves with a distinct zonation pattern.

The new Geranium can be compared to the cultivar, 'BSR-233 Bright Coral' (disclosed in U.S. Plant Pat. No. 8,288). However, in side-by-side comparisons conducted by the Inventor in Arroyo Grande, Calif., plants of the new Geranium differ from plants of the cultivar 'BSR-233 Bright Coral' in the following characteristics:

1. Plants of the new Geranium are more compact than plants of the cultivar 'BSR-233 Bright Coral'.

2. Leaves of the new Geranium have a distinct zonation pattern whereas leaves of plants of the cultivar 'BSR-233 Bright Coral' do not have a zonation pattern.

3. Flower umbels of plants of the new Geranium are spherical whereas flower umbels of plants of the cultivar 'BSR-233 Bright Coral' are hemispherical.

4. Flower color of plants of the new Geranium is brighter than flower color of plants of the cultivar 'BSR-233 Bright Coral'.

A detailed comparison of plants of the cultivar 'BFP-1520' and the cultivar 'BSR-233 Bright Coral' appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in a colored reproduction of this type. The photograph comprises a top perspective view of a typical plant of 'BFP-1520'. Flower and foliage colors in the photograph may appear different from the actual colors due to light reflectance.

DETAILED BOTANICAL DESCRIPTION

The cultivar 'BFP-1520' has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 22° C. and night temperatures about 18° C.

In the following description, color references are made to The Royal Horticultural Society Colour Chart except where general terms of ordinary dictionary significance are used.

Botanical classification: *Pelargonium×hortorum* cultivar 'BFP-1520'.

Parentage:

*Male parent.*—Proprietary *Pelargonium×hortorum* selection 6762-1.

*Female parent.*—Proprietary *Pelargonium×hortorum* selection 6875-8.

Propagation:

*Type cutting.*—Terminal cuttings.

*Time to initiate roots.*—About 7 days at temperatures about 18° C.

*Time to develop roots.*—About 21 days at temperatures about 18° C.

*Rooting habit.*—Fibrous and freely branching.

Plant description:

*General appearance.*—Upright and rounded growth habit. Appropriate for 10 and 12.5-cm containers. About nine weeks are required to produced a finished 10-cm container from a rooted cutting.

*Growth and branching habit.*—Basally branching with about two lateral branches at the base.

*Plant height base of plant to top of leaf plane.—About* 23 cm.

*Plant width.*—About 17.6 cm.

*Lateral branches.*—Length: About 10 cm. Internode length: About 2.5 cm. Color: 146C.

*Foliage description.*—Leaves simple, generally symmetrical, abundant, opposite. Quantity of leaves per lateral branch: About 12. Length: About 5 cm. Width: About 8.2 cm. Shape: Reniform with rounded apex, cordate base, and crenate margin. Texture: Thick, both surfaces pubescent. Color: Fully expanded foliage, upper surface: 137A with zonation pattern, 139A in color, about 1.3 cm wide. Fully expanded foliage, lower surface: 137C. Petiole: Length: About 6.5 cm. Diameter: About 2.8 mm. Color: 137A.

Flower description:

*Flower type and habit.*—Bright coral pink-colored flowers. Very freely and continuously flowering. Flowers arranged in spherical umbels arising from apical leaf axils. Umbels displayed above or beyond the foliage. Usually about five umbels per plant. Flowers semi-double and round. Umbels persistent.

*Flowering season.*—Year-round under greenhouse conditions. In the garden, flowering is continuous from spring through summer.

*Umbels.*—Number of flowers per umbel: About 29. Diameter: About 10.5 cm. Height: About 6.8 cm.

*Flowers.*—Diameter: About 4.8 cm. Depth (height): About 1.5 cm.

*Flower buds.*—Length: About 1.35 cm. Diameter: About 8.5 mm. Shape: Spherical.

*Petals.*—Quantity: Five, overlapping. Usually about six petaloids per flower. Length: About 2.4 cm. Width: About 2.2 cm. Shape: Obovate with rounded apex and entire margin. Texture: Dull, smooth. Color: Fully opened, upper surface: 52A. Fully opened, lower surface: 52B.

*Petaloids.*—Irregular in shape with very narrow white, 155A, base; about 1 cm in length and about 2 mm in width; 52A in color.

*Peduncle* (*umbel stem*).—Length: About 15.8 cm. Strength: Strong. Angle: Mostly erect or slightly angled. Texture: Pubescent. Color: 137A with streaks of 184A.

*Pedicel* (*individual flower stem*).—Length: About 3.7 cm. Strength: Strong. Angle: Upright or outward. Texture: Pubescent. Color:144A overlaid with 182A becoming more predominately red, 182A, with age.

*Reproductive organs.*—Androecium: Anther size: About 2.5 mm. Amount of pollen: Moderate. Pollen color: 31A. Gynoecium: Ovary color: Green.

Disease resistance: Under commercial conditions, resistance to pathogens has not been observed.

Seed development: Seed production has not been observed.

CHART A

| CHARACTERISTIC | 'BFP-1520' | 'BSR-233 BRIGHT CORAL' |
|---|---|---|
| PLANT HEIGHT | About 23 cm | About 27 cm |
| PLANT WIDTH | About 17.6 cm | About 18.4 cm |
| LEAF LENGTH | About 5 cm | About 4.8 cm |
| LEAF WIDTH | About 8.2 cm | About 8 cm |
| LEAF COLOR, MATURE, UPPER SURFACE | 137A with zonation pattern, 139A | 131C, no zonation pattern |
| LEAF COLOR MATURE, LOWER SURFACE | 137C | 131D |
| PETIOLE COLOR | 137A | 131C |
| UMBEL FORM | Spherical | Hemispherical |
| PETAL COLOR, UPPER SURFACE | 52A | 50A |
| PETAL COLOR, LOWER SURFACE | 52B | 48B |
| PEDICEL LENGTH | About 3.7 cm | About 2.8 cm |
| POLLEN COLOR | 31A | 28A |

It is claimed:

1. A new and distinct cultivar of Geranium plant named 'BFP-1520', as illustrated and described.

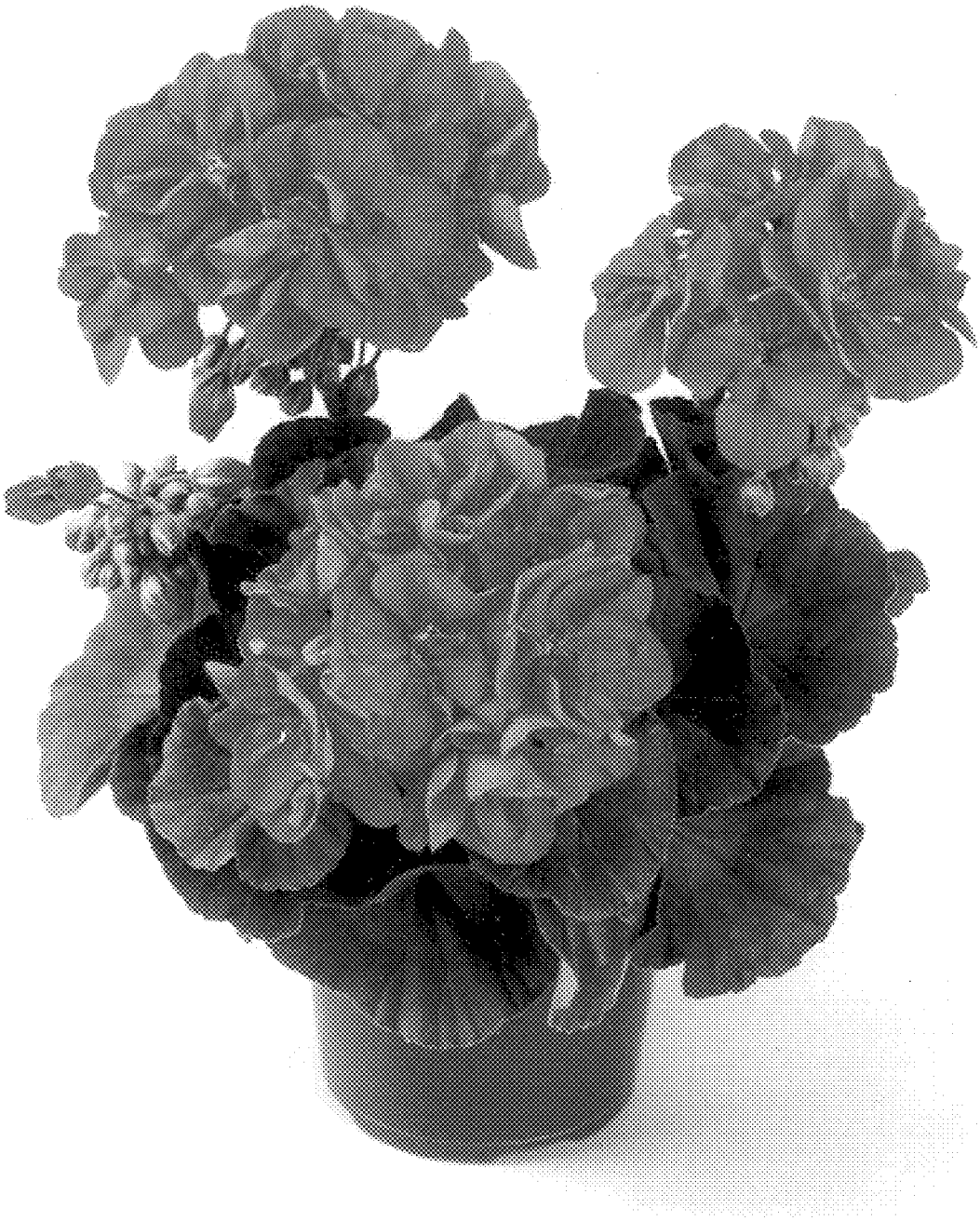

* * * * *